US00PP16022P2

(12) United States Plant Patent
Olesen et al.

(10) Patent No.: US PP16,022 P2
(45) Date of Patent: Oct. 4, 2005

(54) ***CLEMATIS* PLANT NAMED 'EVIPO031'**

(50) Latin Name: *Clematis viticella*
Varietal Denomination: EVIPO031

(75) Inventors: Mogens N. Olesen, Fredensborg (DK); Raymond J. Evison, St. Sampsons (GB)

(73) Assignee: Poulsen Roser A/S, Fredensborg (DK)

( * ) Notice: Subject to any disclaimer, the term of this patent is extended or adjusted under 35 U.S.C. 154(b) by 57 days.

(21) Appl. No.: 10/897,896

(22) Filed: Jul. 23, 2004

(51) Int. Cl.[7] ..... A01H 5/00
(52) U.S. Cl. ..... Plt./228
(58) Field of Search ..... Plt./228

*Primary Examiner*—Kent Bell

(57) ABSTRACT

A new *Clematis* cultivar which is well suited to propagation in glasshouses. With a tall growth habit, profuse, light violet flowers and continuous summer flowering. The variety successfully propagates from softwood cuttings and is suitable for cultivation in commercial glasshouses. This new and distinct variety has shown to be uniform and stable in the resulting generations from asexual propagation.

3 Drawing Sheets

Botanical classification: Genus—*Clematis*. Species—*viticella*.
Variety denomination: 'EVIPO031'.

SUMMARY OF THE DISCOVERY

The present invention constitutes a new and distinct variety of *Clematis* which originated as a chance seedling of unknown parents. The new variety is named 'EVIPO031'.

The objective of the selection of this *Clematis* variety for commercial glasshouse and nursery culture was to create a new and distinct variety with unique qualities that this variety has:

1. Profuse light violet flowers;
2. Reliable and repeatable production plant;
3. Summer flowering;
4. Improved disease resistance.

These qualities required improvement in *clematis* varieties that were in commercial cultivation and the objectives have been substantially achieved in the new variety, as evidenced by the unique combination of characteristics that are present in 'EVIPO031', which distinguish it from all other varieties of which we are aware.

Evaluations of the seedling plant were conducted in a controlled environment. As a result, 'EVIPO031' was selected by Raymond J. Evison and Mogens N. Olesen in their *Clematis* development program in Domarie Vineries Les Sauvagees, St. Sampsons, Guernsey, Channel Islands, United Kingdom in June 1996.

Asexual reproduction of 'EVIPO031' by cuttings was first done by Raymond J. Evison and Mogens N. Olesen in Domarie Vineries Les Sauvagees, St. Sampsons, Guernsey, Channel Islands, United Kingdom in April 1997. This initial and subsequent asexual propagations have demonstrated that the characteristics of 'EVIPO031' are true to type and are transmitted from one generation to the next.

BRIEF DESCRIPTION OF THE DRAWING

The accompanying color illustrations show as true as is reasonably possible to obtain in color photographs of this type:

FIG. 2.2 Stem showing branching and the attachment of leaves, flowers at various stages of development, and seed cluster;

FIG. 2.3 Flower buds closed and as tepals unfold;

FIG. 2.4 Stem showing attachment of mature and juvenile leaves.

DETAILED DESCRIPTION OF THE VARIETY

Figure 1:
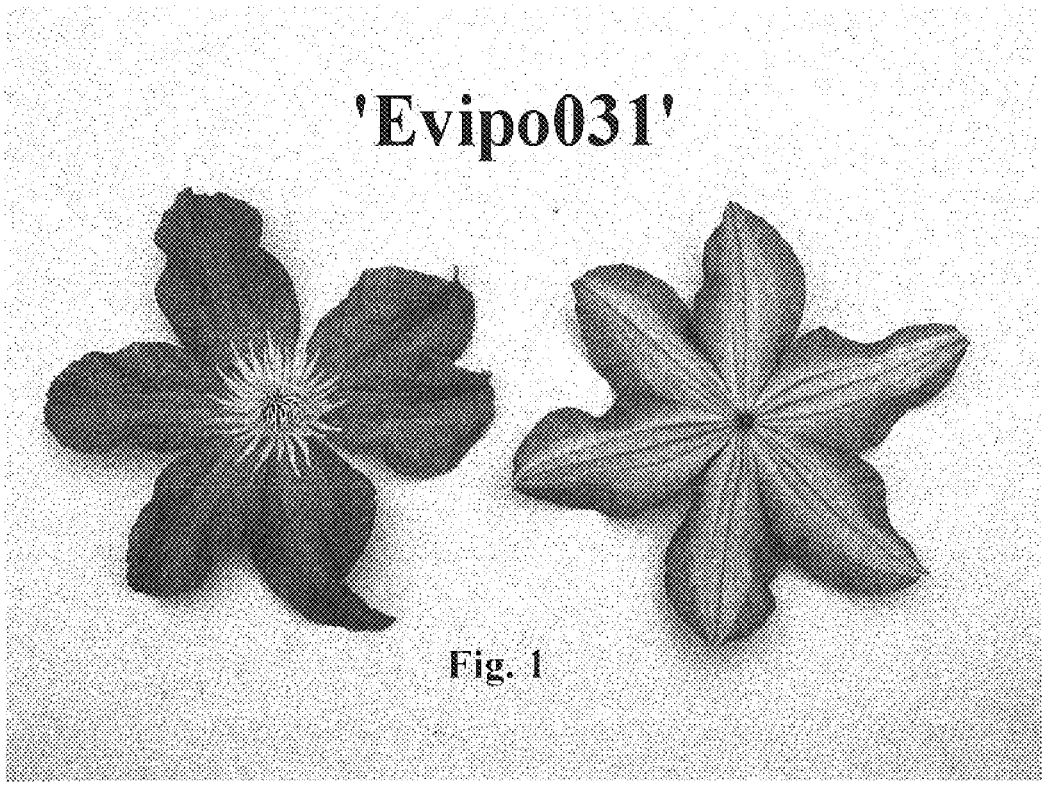
FIG. 1 Enlarged image of open flower, upper and lower surface.

The following is a detailed description of 'EVIPO031', as observed in its growth throughout the flowering period in glasshouses at Domarie Vineries Les Sauvagees, St. Sampsons, Guernsey, Channel Islands, United Kingdom. Observed plants were cultivated for a period of 24 months in 2 liter containers. Certain phenotypical characteristics of the variety may vary under different environmental, cultural, agronomic, seasonal, and climatic conditions. Color references are made using The Royal Horticultural Society (London, England) Colour Chart, 2001.

For a comparison, the nearest existing *Clematis* variety is 'EVIPO001', a patented variety described and illustrated in U.S. Plant patent Application Ser. No. 10/719,750 dated Nov. 21, 2003. Chart 1 details several physical characteristics 'EVIPO031' and the comparison variety.

CHART 1

| | 'EVIPO031' | 'EVIPO001' |
|---|---|---|
| Tepal Count | Normally 6 | 4 to 6 |
| Main tepal color | Violet-Blue Group RHS 90B | Violet Group N88D (no purple tones.) |
| Peduncle aspect | Near horizontal | Horizontal to nodding |
| Foliage | Trifoliate | Normally trifoliate but greater tendency |

CHART 1-continued

| 'EVIPO031' | 'EVIPO001' |
|---|---|
| | to produce simple leaves. |

FLOWER AND FLOWER BUD

Blooming habit: Summer flowering. Normal flowering months are May, June, July, August, September.

Flower bud:

*Size.*—37 mm in length. Bud diameter is 15 mm.

*Bud form.*—Ovate.

*Bud color.*—Yellow-Green Group 144B, proceeding to Violet Group 85B with margins of violet Group 86B as tepals unfold.

Peduncle:

*Aspects.*—Near horizontal.

*Surface.*—Smooth.

*Length.*—100 to 130 mm average length.

*Color.*—Yellow-Green Group 146B.

*Strength.*—Moderately strong.

Receptacle: Absent.

Flower arrangement:

*Location on vine.*—New growth only.

*Borne.*—Compound cyme cluster of 5 flowers.

Flower bloom:

*Size.*—85 to 95 mm in diameter. 20 mm in depth.

*Profile.*—Upon opening: Flowers are flat. After opening: Flowers are flat with tepals reflexing somewhat.

*Tepal color.*—Upon opening: Upper surface is Violet Group 86A in color. After opening: Upper surface is Violet-Blue Group 90B in color. The underside margin is of the same color as the main upper side Violet-Blue Group 90B. The middle zone is slightly lighter Violet-Blue Group 91B with three longitudinal bars of approximate color Purple-Violet Group 80A.

*Variations.*—Violet Group 85D at tepal base.

*Fragrance.*—None.

*Lasting quality on plant.*—10 to 15 days.

*Lasting quality as a cut flower.*—4 to 5 days.

Tepals:

*Quantity.*—Normally 6 tepals, occasionally 5 or 7 tepals observed.

*Size.*—42 to 45 mm in length by 25 to 30 mm wide.

*Shape.*—Individual tepal shape is ovate to elliptical.

*Margin.*—Entire, slight undulation.

*Tepal apex.*—Acute.

*Recurvature of tip.*—Moderately reflexed.

*Persistence.*—After flowers have matured, tepals drop off cleanly.

*Arrangement.*—Tepals are arranged regularly.

Reproductive organs:

*Arrangement.*—Open.

*Pollen.*—Quantity: Scant. Color: Yellow Group 5C.

*Anthers.*—Size: 4 mm in length. Color: Yellow Group 7A. Quantity: 45 to 60.

*Filaments.*—Color: White Group N155A. Length: 9 mm.

*Pistils.*—Quantity: 35 to 42.

*Stigmas.*—Inferior to anthers, becoming superior as the flower opens.

*Styles.*—Color: White Group 155B with base covered with feathery sheath of Greyed-Yellow Group 162B. Length: 8 to 12 mm.

Seed head characteristics:

*Size.*—Approximately 50 mm in diameter at the base.

*Shape.*—Tear shaped with approximately 8 mm diameter with elongated plumule.

PLANT

Plant form: Climbing.

Size: Seasons growth attains 2 to 2.5 meters in height. Average spread is 1 to 1.5 meters.

Hardiness: Trials to date show the variety is cold tolerant to USDA Cold Hardiness Zone 3.

Stems:

*Color.*—Young wood: Greyed-Orange 177A. Older wood: Greyed-Orange 166B.

*Internodes.*—Shape: Cylindrical. Length: 110 mm to 140 mm.

*Surface.*—Young wood: Smooth and pubescent. Older wood: Smooth and pubescent.

Plant foliage:

*Leaf characteristics.*—Deciduous.

*Mature leaf form.*—Trifoliate.

*Compound leaf size.* —90 to 125 mm (l)×100 to 120 mm (w).

*Abundance.*—Generally, there are 4 leaves per 120 mm of stem.

*Color.*—Upper surfaces of mature leaves: Green Group 143A. Lower surfaces of mature leaves: Green Group 143C. Upper surfaces of new foliage: Yellow-Green Group 144B. Lower surfaces of new foliage: Yellow-Green Group 144D.

Plant leaves and leaflets:

*Stipules.*—Absent.

*Petioles.*—Average length: 65 to 100 mm. Color: Yellow-Green 144D. Clasping: By leaf petiole.

*Petioloule.*—Length: 10 to 15 mm. Color: Yellow-Green Group 144D.

*Leaf edge.*—Terminal leaflet margin is entire.

*Leaflet shape.*—General shape: Ovate. Base: Rounded. Apex: Acute.

*Leaflet size.*—50 to 60 mm in length by 30 to 40 mm wide.

*Leaflet texture.*—Smooth. Upper side: Smooth. Lower side: Smooth. Pubescence: Not observed. Thickness: Moderate. Glossiness: Moderately Glossy Finish.

Disease resistance: Subject to any disease that normally attacks the species, however the variety is more tolerant to Botrytis, *Phoma clematadina*, and root diseases such as Theilaviopsis than some *Clematis*.

We claim:

1. A new and distinct variety of *clematis* plant named 'EVIPO031', described and illustrated herein, due to its abundant light violet flowers, attractive long-lasting foliage and repeatable flowering under glasshouse conditions, suitability for production from softwood cuttings in pots, durable flowers and foliage which make the variety suitable for distribution in the floral industry.

* * * * *

Figure 2:
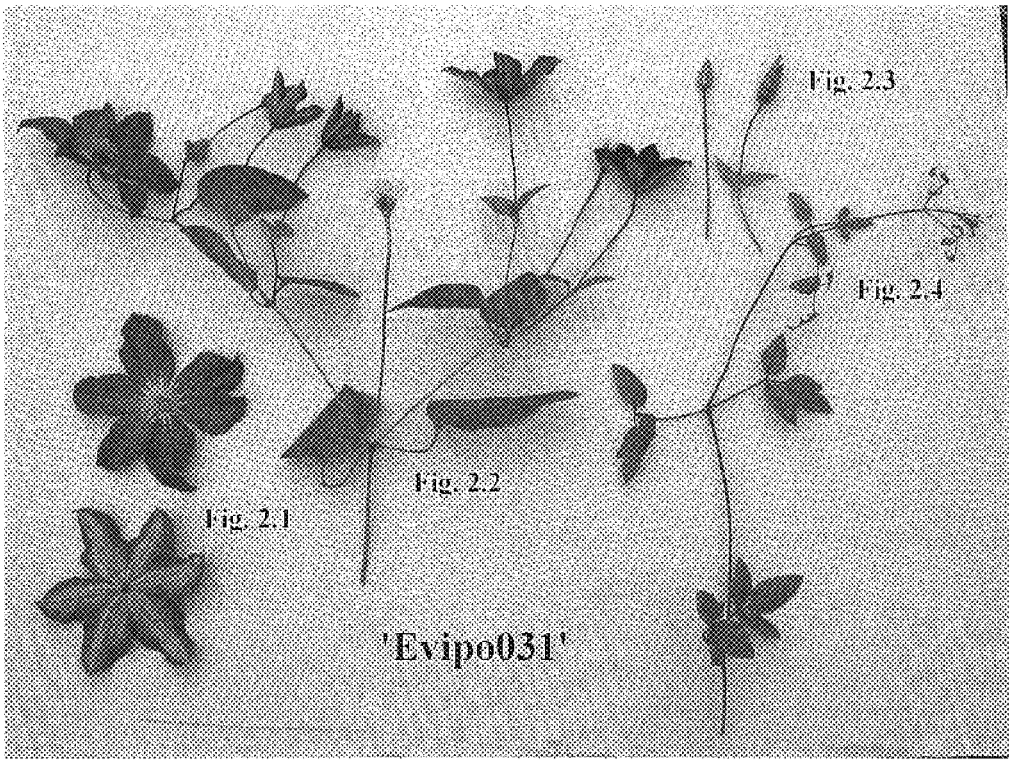
FIG. 2.1 Open flower, upper and lower surface.
Figure 3:
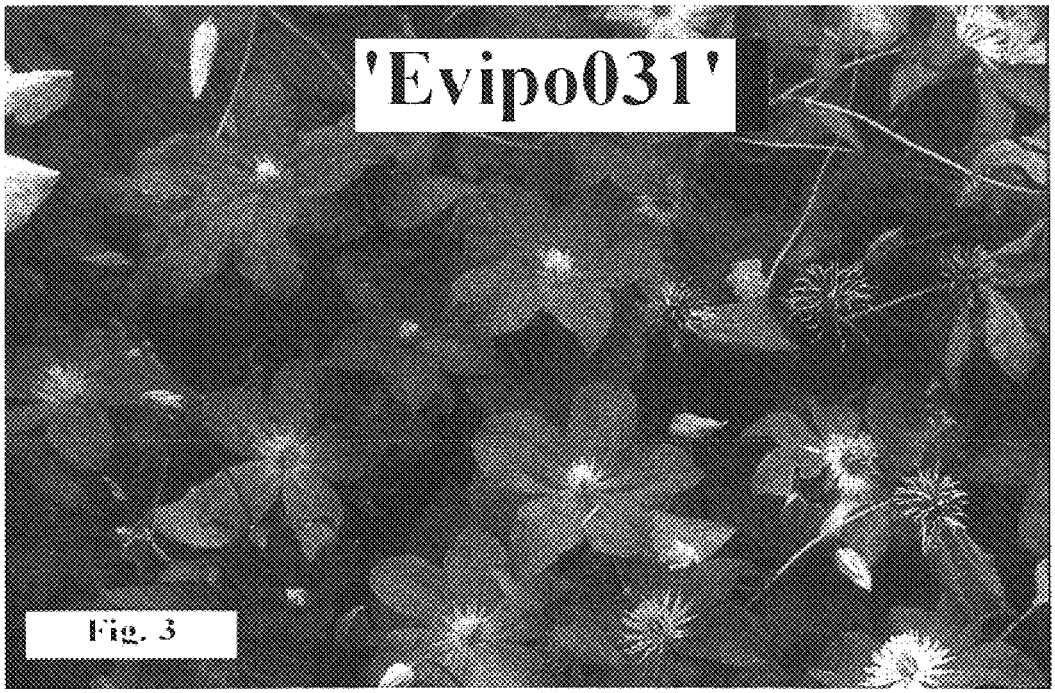
FIG. 3 Leaves, cluster of flowers showing attitude, and seed heads.

Fig. 2.3
Fig. 2.4
Fig. 2.2
Fig. 2.1
'Evipo031'